United States Patent [19]

Herring, Jr.

[11] Patent Number: 5,394,754
[45] Date of Patent: Mar. 7, 1995

[54] APPARATUS FOR TESTING A HEM FLANGE AND METHOD FOR SAME

[75] Inventor: James M. Herring, Jr., Rochester Hills, Mich.

[73] Assignee: The Budd Company, Troy, Mich.

[21] Appl. No.: 18,775

[22] Filed: Feb. 17, 1993

[51] Int. Cl.⁶ .............................................. G01N 3/08
[52] U.S. Cl. ...................................... 73/826; 73/834; 73/841; 73/845; 73/831
[58] Field of Search ................ 73/827, 834, 837, 831, 73/833, 845, 846, 842, 850, 851

[56] References Cited

U.S. PATENT DOCUMENTS

| | | | |
|---|---|---|---|
| 2,453,576 | 11/1948 | Jacob | 73/845 |
| 4,027,529 | 6/1977 | Olsen | 73/827 |
| 4,380,174 | 4/1983 | Tanenbaum | 73/842 |
| 4,861,407 | 8/1989 | Volkmann et al. | |
| 4,904,328 | 2/1990 | Beecher et al. | |
| 4,968,383 | 11/1990 | Volkmann et al. | |
| 4,978,407 | 12/1990 | Ardissone | |
| 5,176,028 | 1/1993 | Humphrey | 73/842 |

FOREIGN PATENT DOCUMENTS

| | | | |
|---|---|---|---|
| 136892 | 8/1979 | Germany | 73/827 |
| 276483 | 10/1970 | U.S.S.R. | 73/842 |

*Primary Examiner*—Hezron E. Williams
*Assistant Examiner*—Nashmiya Ashraf
*Attorney, Agent, or Firm*—Harness, Dickey & Pierce

[57] ABSTRACT

A test apparatus for testing hem flanges that join automotive body panels is provided. This testing apparatus operates by engaging a hook member with a first body panel such that the first body panel is maintained in a held relationship with respect to the hook member. A ram member then extends from the testing apparatus and engages with and loads a second automotive body panel member. As a result, a tensile load is applied to the hem flange, permitting the hem flange to be analyzed for defective construction.

13 Claims, 3 Drawing Sheets

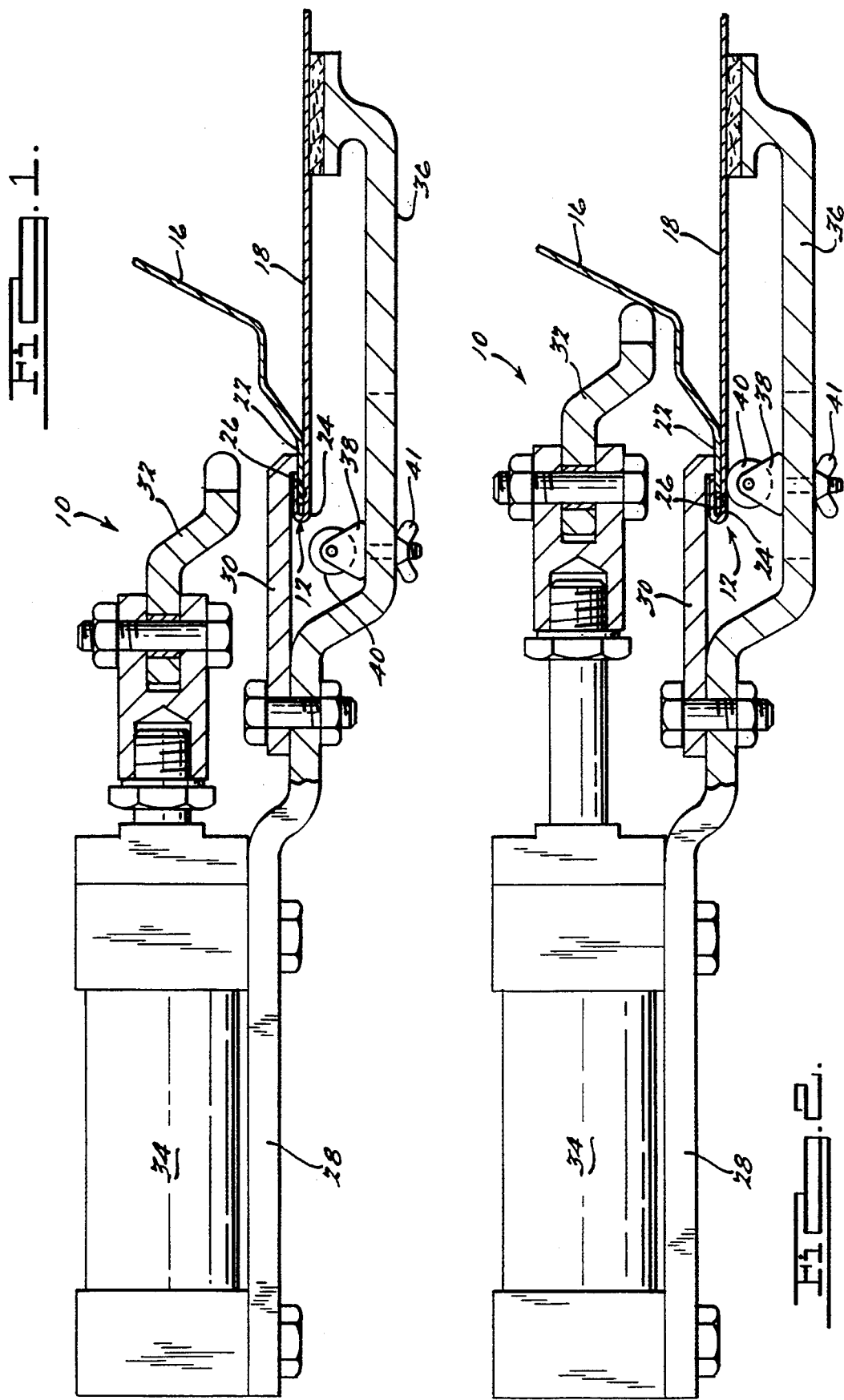

APPARATUS FOR TESTING A HEM FLANGE AND METHOD FOR SAME

BACKGROUND OF THE INVENTION

1. Technical Field

This invention relates generally to a hem flange testing apparatus and, more particularly, to an apparatus that tests hem flanges on automotive vehicle body panels.

2. Discussion

Hem flanges that connect inner and outer body panels, such as door panels, often utilize a weld to secure the panels to one another. To avoid having to finish the rough exterior surface of such welds, some manufacturers have begun securing panels to one another with adhesives. This eliminates the need for welding and also provides a sealing effect between the panels. To ensure that these hem flanges have been properly adhered, it would be desirable to have a hem flange testing apparatus that could quickly test a hem flange to determine its quality. It would also be desirable if this hem flange testing apparatus was easy to use, compact and provided consistent test results.

SUMMARY OF THE INVENTION

The present invention relates to a hem flange testing apparatus that provides the above mentioned desirable features. The testing apparatus operates by engaging an outer automotive body panel such that the outer panel is maintained in a held relationship with respect to the testing apparatus. The testing apparatus also engages an inner automotive body panel and a load is applied to this inner panel in a direction substantially parallel to a test axis. Accordingly, a tensile load is applied across the hem flange that joins the inner and outer body panel members. While the hem flange is under this tensile load, the hem flange is inspected for any indications of failure. After the inspection is completed, the inner panel is unloaded and the panels are disengaged from the hem flange testing apparatus.

BRIEF DESCRIPTION OF THE DRAWINGS

Additional objects, advantages, and features of the present invention will become apparent from the following description and appended claims, taken in conjunction with the accompanying drawings in which:

FIG. 1 is a side view of the hem flange testing apparatus of the present invention with a portion broken away illustrating the testing apparatus in a disengaged position;

FIG. 2 is a side view of the hem flange testing apparatus of the present invention with a portion broken away illustrating the testing apparatus fully engaged with both the inner and outer door panel members;

DETAILED DESCRIPTION OF THE PREFERRED EMBODIMENT

Figure 3:
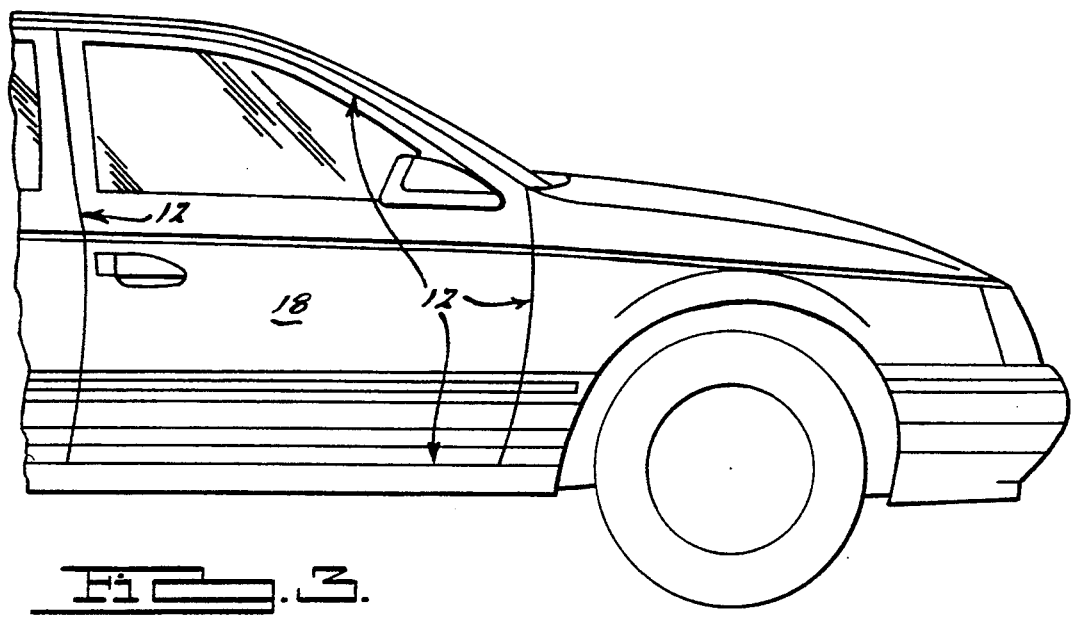
FIG. 3 is a side view of a portion of an automotive vehicle that uses hem flanges to join inner and outer body panels.

Referring now to the drawings, and more particularly to FIG. 1, the hem flange testing apparatus 10 of the present invention is shown. This particular hem flange testing apparatus 10 is utilized to test hem flanges 12 that join inner and outer automotive door panels 16 and 18. As can be seen from FIG. 3, the outer door panel 18 forms the exterior surface of the door and the inner reinforcing door panel 16 extends along the inboard side of the outer door panel 18 in a spaced relationship therewith, as shown in FIGS. 1 and 2. Note, the end portion 24 of the outer door panel 18 extends along find folds over the end portion 22 of the reinforcing panel 16. Accordingly, an inner surface 26 on the outer panel 18 surrounds the end portion 22 of the inner reinforcing panel 16 in abutting engagement therewith. The end portions 22 and 24 of both the inner and outer panels 16 and 18 are affixed to one another by adhesive bonding or the like, thereby creating the hem flange 12. The unique hem flange testing apparatus 10 of the present invention is utilized to determine if these types of hem flanges 12 have the requisite structural integrity to withstand loads imparted by operation of the automotive vehicle.

The hem flange testing apparatus 10 essentially has a base portion 28, along with two members that engage the body panels 16 and 18 and displace them relative to one another. As shown in FIGS. 1 and 2, the first member is essentially a hook-shaped member 30 that rigidly extends from the base portion 28 and engages the folded over portion 24 of the outer body panel 18. Accordingly, the outer body panel 18 is in a held relationship with respect to this hook-shaped member 30 and is prevented from moving in a direction away from the hook-shaped member 30. The second member is a hydraulically or pneumatically actuated ram member 32 that extends from the base portion 28 and engages the inner reinforcing panel member 16. As shown in FIGS. 1 and 2, this ram member 32 extends from a hydraulic or pneumatic cylinder 34 that is rigidly affixed to the base portion 28 and is therefore fixed with respect to the hook-shaped member 30. Thus, when the ram member 32 is outwardly actuated and it engages a portion of the inner reinforcing panel member 16, the inner member 16 is loaded, thereby applying a tensile load to the hem flange 12.

Figure 5:
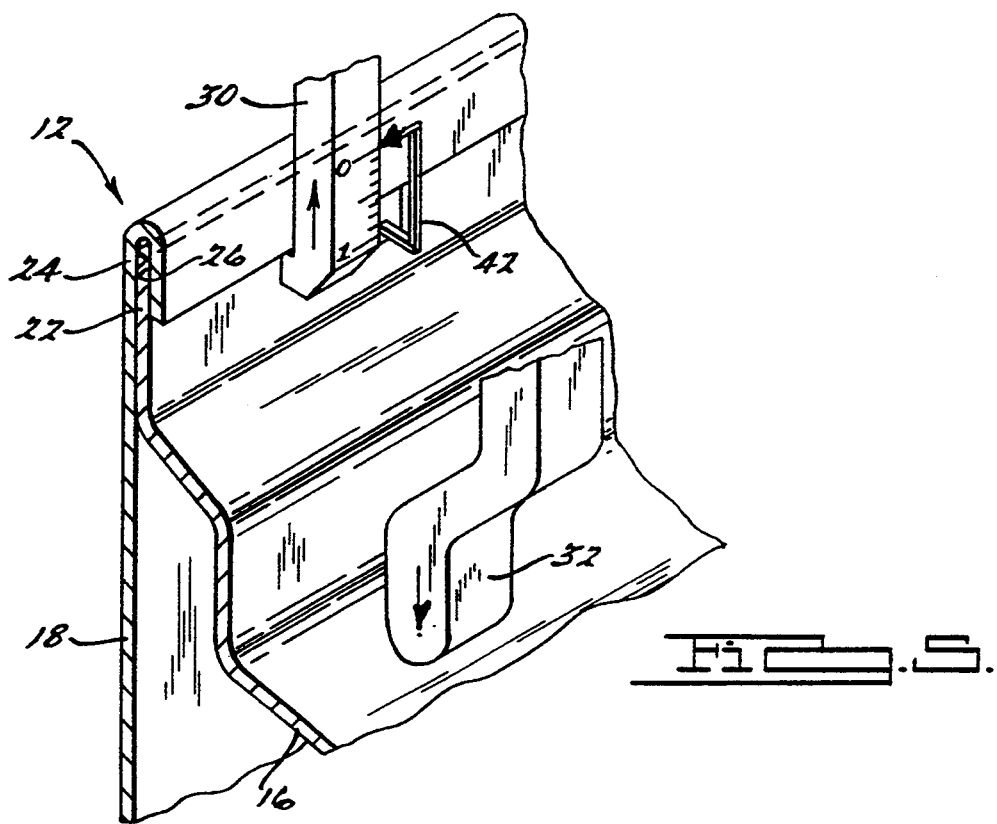
FIG. 5 is a perspective view of a portion of the inner and outer automotive door panel members being tested by the hem flange testing apparatus of the present invention.
Figure 6:
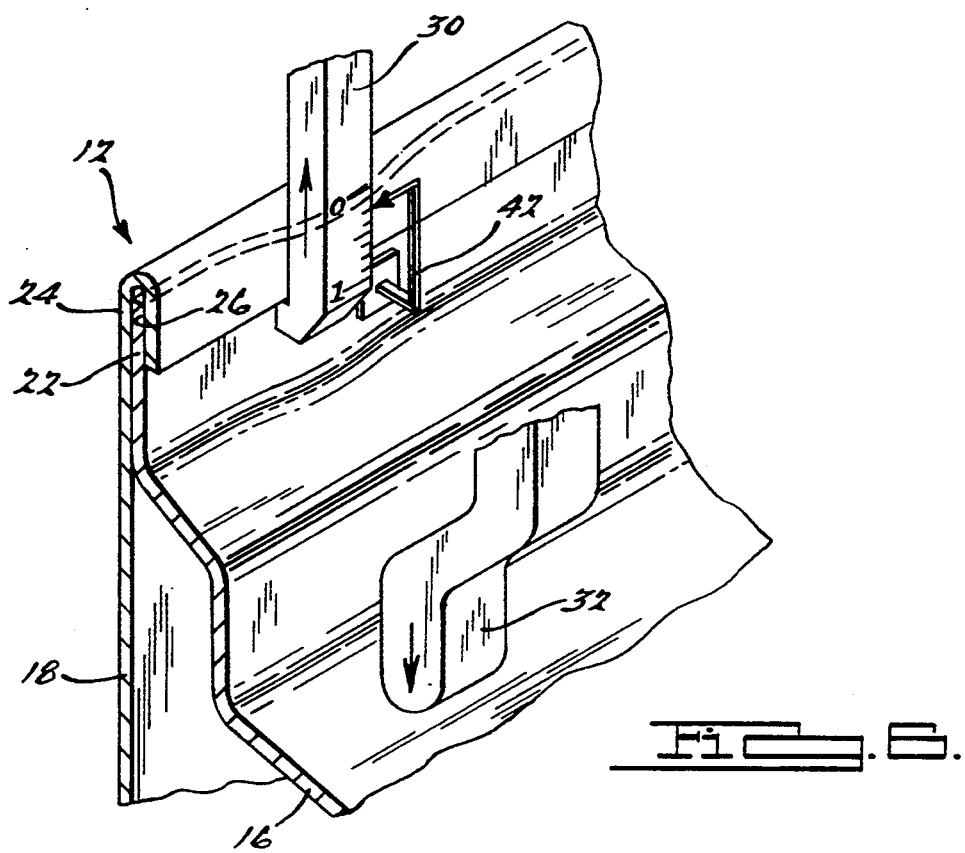
FIG. 6 is a perspective view of a portion of the inner and outer automotive door panel members being tested by the hem flange testing apparatus of the present invention, illustrating the inner reinforcing member withdrawing from the folded over portion of the outer reinforcing member.

As described above, the hem flange testing apparatus 10 of the present invention utilizes the ram member 32 and the hook-shaped member 30 to apply a preselected tensile load across the hem flange 12. Ideally, this tensile load would pass through the test axis A—A (FIG. 4) which extends directly through the middle of the hem flange 12, parallel to the end portion 22 of the inner reinforcing member 16. Such a tensile load would cause the end portion 22 of the inner reinforcing member 16 to be loaded in a direction parallel to the folded over portion 24 of the outer door panel 18 in contact therewith. Thus, if the hem flange 12 is defective, the end portion 22 of the inner reinforcing member 16 would withdraw from the folded over portion 24 of the outer door panel 18, as shown in FIG. 6. On the other hand, if the hem flange testing apparatus 10 is utilized to test a properly manufactured hem flange 12, the tensile load across the hem flange 12 will not cause the inner reinforcing member 16 to withdraw from the folded over portion 24 of the outer panel member 18, as shown in FIG. 5.

Figure 4:
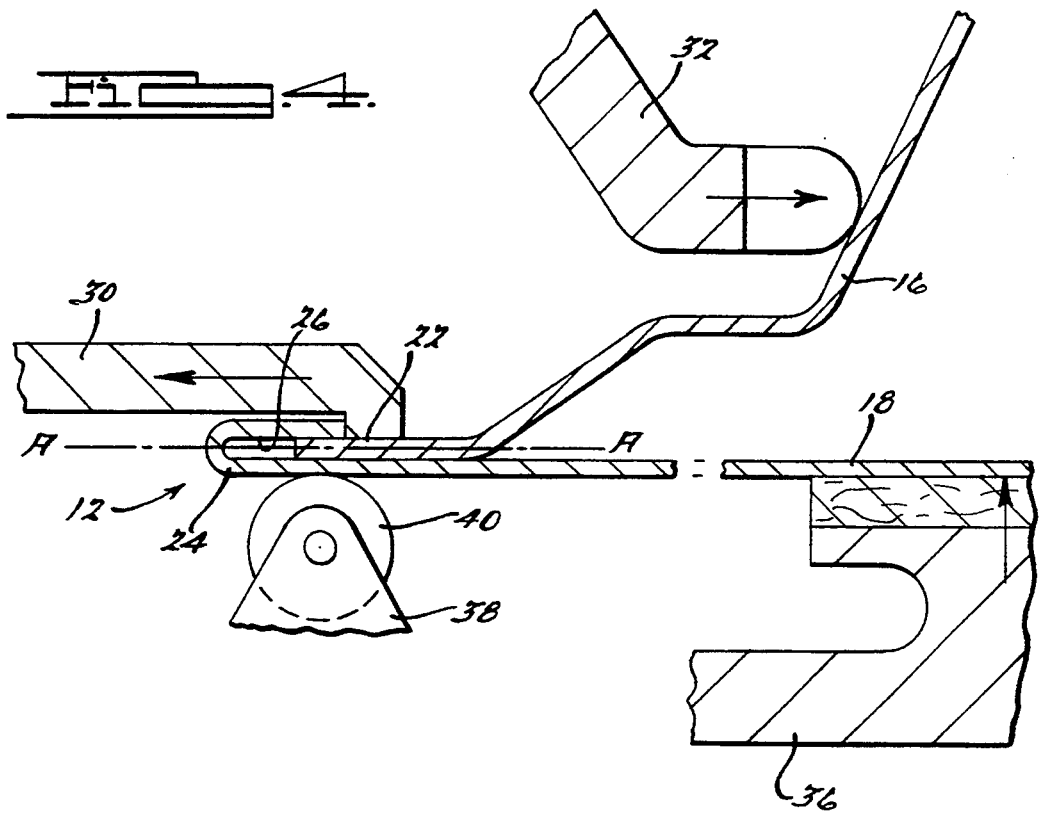
FIG. 4 is a diagrammatic view of the various loads being applied to both the inner and outer door panel members during testing of a hem flange in accordance with the principles of the present invention.

As best shown in FIG. 4, the loads applied by the hook-shaped member 30 to outer member 18 and the ram member 32 to inner member 16 are parallel to the test axis A—A, however, these loads are applied at two different distances from the test axis A—A. As a result, a moment is created across both the inner and the outer door panel members 16 and 18, causing the panel members 16 and 18 to rotate away from the ram member 32. To counteract this moment, a support member 36 extends from the base portion 28 of the testing apparatus 10 to support the outer door panel 18 and prevent both panels 16 and 18 from rotating while being tested. As can be seen from FIG. 4, when the hook member 30 and rain member 32 apply loads to the door panels 16 and 18, the support member 36 applies a reaction load that balances the moments and forces being applied to the panels 16 and 18. Consequently, the inner and outer door panels 16 and 18 are kept in a state of equilibrium and prevented from distorting while being tested.

In addition to the support member 36, a second retractable support member 38 can be utilized to stabilize the inner and outer door panels 16 and 18 on the testing apparatus 10. As best shown in FIGS. 1 and 2, this retractable support member 38 preferably has a wheel-like member 40 that is slid into engagement with the hem flange 12 thereby trapping it between the shank portion of the hook member 30 and the retractable support member 38. The retractable support member 38 slidingly engages the support member 36 such that it can be slid into place manually and held by a wing nut 41, or the like. By trapping the hem flange 12 between the hook member 30 and the retractable support member 38, the folded over portion 24 of the outer door panel 18 is prevented from slipping off the relatively thin hook portion of the hook member 30. In addition, the retractable support member 38 prevents the hem flange 12 from being improperly mounted on the hook member 30 and insures proper alignment therewith.

In operation, the hem flange testing apparatus 10 of the present invention is utilized as follows. Either the inner and outer door panels 16 and 18, or the hem flange testing apparatus 10, are secured by way of a clamp, jig, or the like (not shown). Once the testing apparatus 10, or the inner and outer door panels 16 and 18, are secured, the other is placed into position such that the hook member 30 engages the folded over portion 24 of the outer body panel member 18. Thereafter, tile retractable support member 38 is moved into engagement with the hem flange 12, as shown in FIG. 2. The ram member 32 is also moved into engagement such that it loads the inner reinforcing panel member 16, as shown in FIG. 2. If the inner member 16 withdraws from the folded over portion 24 of the outer member 18, as shown in FIG. 6, the hem flange 12 has failed the test. If the inner member 16 does not withdraw from the folded over portion 24, as shown in FIG. 5, the hem flange 12 has passed the test. Note, withdrawal of the inner member 16 can be measured by a conventional measuring device 42 to obtain accurate test results, as shown diagrammatically in FIGS. 5 and 6. In any event, after determining whether or not the hem flange 12 has failed the test, the ram member 32 and the retractable support member 38 are retracted and the panels 16 and 18 are removed from the testing apparatus 10. Accordingly, the hem flange testing apparatus 10 of the present invention provides an easy to use, compact and reliable method for testing automotive body panel hem flanges.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

It is claimed:

1. A method for testing a hem flange that joins a first panel with a second panel, said first panel having an end portion which is folded over an end of said second panel, said method comprising the steps of:
   a) engaging said folded over end of said first panel with a hook member of a hem flange testing apparatus;
   b) supporting said first panel;
   c) using a movable member to push said second panel away from said hook member thereby creating a tensile load in said hem flange generally along a test axis;
   d) inspecting said hem flange; and
   e) unloading said second panel.

2. The method of claim 1 wherein said step d) comprises checking for displacement of said first and second panels relative to one another.

3. The method of claim 1 wherein said step d) comprises utilizing measuring means for measuring displacement of said first and second panels relative to one another.

4. The method of claim 1 wherein said step a) comprises further engaging said hem flange with a retractable support member, thereby locking said panels with respect to said hook member of said testing apparatus.

5. The method of claim 1 wherein the first and second panels respectively comprise outer and inner automotive door panels.

6. A testing apparatus for testing hem flanges that join a first panel with a second panel, the first panel having an end portion which is folded over an end of the second panel, said testing apparatus comprising:
   a) first engaging means for engaging the folded over end of a first panel with a hook member such that said first panel remains stationary when said first panel is subject to loads in a direction substantially parallel to a test axis;
   b) second engaging means for engaging said second panel that is coupled to said first panel by said hem flange, said second engaging means coupled to said first engaging means such that loads can be applied to said panels by moving said second engaging means relative to said first engaging means; and
   c) loading means for loading said panels by moving said second engaging means relative to said first engaging means such that said hem flange is subject to a tensile load generally along said test axis.

7. The testing apparatus of claim 6 wherein said second engaging means engages an inner automotive body panel and said first engaging means engages an outer automotive body panel that is folded over an end portion of said inner body panel such that when said second engaging means moves relative to said first engaging means, said tensile load is applied to said hem flange.

8. The testing apparatus of claim 6 wherein said loading means is an actuating cylinder mounted to said first engaging means that loads said second panel by moving said second engaging means relative to said first engaging means.

9. The testing apparatus of claim 6 wherein said testing apparatus further comprises a first support member that engages said first panel, thereby preventing distortion of said first panel when said tensile load is applied.

10. The testing apparatus of claim 6 wherein said testing apparatus further comprises a retractable support member that engages said panels adjacent to the hem flange being tested, thereby locking said panels into a test position.

11. The testing apparatus of claim 10 wherein said retractable support member utilizes a wheel means to engage said panels 12. The testing apparatus of claim 6 wherein said testing apparatus further comprises means for measuring movement of said second panel relative to said first panel.

13. An apparatus for testing a hem flange that joins a first panel with a second panel, the first panel having an end portion which is folded over an end of the second panel, said apparatus comprising:
- an elongated base;
- support means on one end of the base for supporting a surface of the first panel spaced from the hem flange;
- a cylinder mounted to an opposite end of the base, said cylinder having a movable ram extending therefrom;
- a hook member having a downturned lip for engaging the folded over end portion of the hem flange, the hook member being connected to the base;
- retractable means carried by the base between the hook member and support means, said retractable means clamping the hem flange in abutting engagement with the hook member when the retractable support is in an operable position; and
- said ram being movable by the cylinder to engage the second panel and create a tensile load on the hem flange to thereby test the integrity thereof.

* * * * *